(12) United States Patent
Schwertfeger et al.

(10) Patent No.: US 6,280,744 B1
(45) Date of Patent: Aug. 28, 2001

(54) USE OF INORGANIC AEROGELS IN PHARMACY

(75) Inventors: Fritz Schwertfeger, Frankfurt; Andreas Zimmermann, Griesheim; Harald Krempel, Seeheim-Jugenheim, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 08/894,362

(22) PCT Filed: Feb. 22, 1996

(86) PCT No.: PCT/EP96/00731

§ 371 Date: Sep. 22, 1997

§ 102(e) Date: Sep. 22, 1997

(87) PCT Pub. No.: WO96/25950

PCT Pub. Date: Aug. 29, 1996

(30) Foreign Application Priority Data

Feb. 22, 1995 (DE) ................................. 195 06 141

(51) Int. Cl.⁷ ............................... A61K 9/14; A61K 9/16; A61K 33/10; A61F 2/02
(52) U.S. Cl. ................... 424/400; 424/421; 424/422; 424/691; 424/724
(58) Field of Search ................ 424/434, 52, 49, 424/44, 440, 400, 421, 422, 691, 724; 514/23; 423/338

(56) References Cited

U.S. PATENT DOCUMENTS

| 4,123,511 | 10/1978 | Heintze | 514/63 |
|---|---|---|---|
| 4,185,088 | 1/1980 | Wagener | 424/497 |
| 4,411,885 | 10/1983 | Barels | 424/52 |
| 4,859,709 | 8/1989 | Rawlins | 514/770 |
| 4,954,327 | * 9/1990 | Blount | 423/338 |
| 5,409,902 | * 4/1995 | Carson et al. | 514/23 |
| 5,670,138 | * 9/1997 | Venema et al. | 424/52 |
| 5,830,480 | * 11/1998 | Ducheyne et al. | 424/400 |

FOREIGN PATENT DOCUMENTS

| 1302895 | 6/1992 | (CA) . |
|---|---|---|
| 26 52 163 | 1/1978 | (DE) . |
| 0163178 | 12/1985 | (EP) . |
| 0255000 | 2/1988 | (EP) . |
| 1572718 | 7/1980 | (GB) . |
| WO 95/01165 | 1/1995 | (WO) . |

OTHER PUBLICATIONS

Database WPI, AN 94–089171; 1994.

\* cited by examiner

Primary Examiner—Carlos A. Azpuru
(74) Attorney, Agent, or Firm—Frommer Lawrence & Haug LLP

(57) ABSTRACT

The invention relates to the use of inorganic aerogels as an auxiliary and/or excipient for pharmaceutical active compounds and/or preparations.

27 Claims, No Drawings

USE OF INORGANIC AEROGELS IN PHARMACY

This application is a 371 of PCT/EP96/00731 filed Feb. 22, 1996 which claims priority from DE 1905061461 filed Feb. 22, 1995.

The invention relates to the use of inorganic aerogels as an auxiliary and/or excipient for pharmaceutical active compounds and/or preparations.

Aerogels, in particular those having porosities of over 60% and densities of under 0.6 g/cm$^3$, have an extremely low thermal conductivity and are therefore used as a heat-insulating material as described, for example, in EP-A-0 171 722. Moreover, the use of aerogels for Cerenkov detectors on the basis of their refractive index, which is very low for solids, is known. Furthermore, on account of the particular acoustic impedance of the aerogels a possible use as matching impedance means, for example in the ultrasonic field, is described in the literature.

Aerogels in the wider sense, i.e. in the sense of "gel with air as a dispersant", are prepared by drying a suitable gel. The term "aerogel" in this sense includes aerogels in the narrower sense, xerogels and cryogels. A dried gel is designated as an aerogel in the narrower sense here if the liquid of the gel is removed to the greatest possible extent at temperatures above the critical temperature and starting from pressures above the critical pressure. If the liquid of the gel, however, is removed subcritically, for example with formation of a liquid/vapor boundary phase, then the resulting gel is designated as a xerogel.

When using the term aerogels in the present application, we are dealing with aerogels in the wider sense, i.e. in the sense of "gel with air as a dispersant".

Moreover, the aerogels can be basically subdivided into inorganic and organic aerogels.

Inorganic aerogels have been known since 1931 (S. S. Kistler, Nature 1931, 127, 741). Since then, aerogels have been prepared from all sorts of starting materials. It was possible here to prepare, for example, $SiO_2$, $Al_2O_3$, $TiO_2$, $ZrO_2$, $SnO_2$, $Li_2O$, $CeO_2$ and $V_2O_5$ aerogels, and mixtures of these (H. D. Gesser, P. C. Goswami, Chem. Rev. 1989, 89, 756 ff). For some years, organic aerogels made of all sorts of starting materials, such as, for example, from melamine formaldehyde, have also been known (R. W. Pekala, J. Mater, Sci. 1989, 24, 3221).

Inorganic aerogels can be prepared here in all sorts of different ways.

For example $SiO_2$ aerogels can be prepared by acidic hydrolysis and condensation of tetraethyl orthosilicate in ethanol. In this process a gel results which can be dried with retention of the structure by supercritical drying. Preparation processes based on this drying technique are known, for example, from EP-A-0 396 076 or WO 92/03378.

An alternative is offered by a process for the subcritical drying of $SiO_2$ gels if these are reacted with a chlorine-containing silylating agent before drying. The $SiO_2$ gel can be obtained here, for example, by acidic hydrolysis of tetralkoxysilanes in a suitable organic solvent by means of water. After replacement of the solvent by a suitable organic solvent, the gel obtained is reacted in a further step with a silylating agent. The $SiO_2$ gel resulting here can then be dried in the air from an organic solvent. Aerogels with densities of under 0.4 g/cm$^3$ and porosities of over 60% can thus be achieved.

The preparation process based on this drying technique is described in detail in WO 94/25149.

The gels described above can moreover be treated with tetraalkoxysilanes and aged before drying in the alcoholic-aqueous solution in order to increase the gel network strength, e.g. as disclosed in WO 92/20623.

Furthermore, the $SiO_2$ gel can also be prepared on the basis of waterglass. The preparation process based on this technique is known from DE-A-43 42 548.

German patent application 19502453.2 moreover describes the use of chlorine-free silylating agents.

The aerogels obtained by supercritical drying are, depending on the process specifically used, hydrophilic or, in the short term, hydrophobic. In the long-term, however, they are hydrophilic.

This can be avoided by a hydrophobization step during the supercritical drying. Such a process is known from EP-A-0 396 076.

Due to their preparation process (silylation before drying), subcritically dried aerogels are permanently hydrophobic.

The use of colloidal silica in therapeutic copper compositions is known, for example, from U.S. Pat. No. 4,123,511.

The use of organic aerogels in medicine is likewise known (WO 95/01165).

It was an object of the present invention to search for novel applications for aerogels.

It has now surprisingly been found that inorganic aerogels are suitable as an auxiliary and/or excipient for pharmaceutical active compounds and/or preparations.

An inorganic aerogel is to be understood in the present application as meaning an aerogel which was prepared based on inorganic materials.

The term "aerogels based on inorganic materials" in particular also includes those aerogels which have been modified, for example, by silylation.

Aerogels mainly comprising $SiO_2$, $Al_2O_3$, $TiO_2$, $ZrO_2$ or mixtures thereof are preferred. Depending on use, these can have hydrophilic and/or hydrophobic surface groups (e.g. OH, OR, R). The preparation of aerogels having hydrophilic and/or hydrophobic surface groups can be carried out here by all processes known to the person skilled in the art. Hydrophilic or hydrophobic $SiO_2$-containing aerogels, in particular $SiO_2$ aerogels, are particularly preferred.

Moreover, it has surprisingly been found that by the choice of a suitable hydrophilic or hydrophobic aerogel appropriate substances with which the aerogel has been loaded can be released in accelerated or delayed form. Furthermore, aerogels can be employed as dispersants for dispersions of solid, liquid or gaseous substances in solid or liquid media. Moreover, hydrophilic or hydrophobic aerogels loaded with hydrophilic and/or hydrophobic substances can be incorporated without problems in hydrophilic and/or hydrophobic, liquid, semisolid or solid media, in particular in order, with the aid of hydrophilic aerogels, to introduce hydrophobic (i.e. lipophilic) substances into liquid and/or semisolid hydrophilic dispersion media, and with the aid of hydrophobic aerogels to introduce hydrophilic substances into liquid, hydrophobic dispersion media. Hydrophobic aerogels, for example, float on hydrophilic, aqueous media, by means of which pharmaceutical excipient systems which float on gastric juice are possible. Furthermore, it is also possible to convert liquid, hydrophilic or hydrophobic substances into solid, freely flowable powders or granules. Problem-free processing, for example to give tablets, capsules or suppositories, is thus possible. Furthermore, with appropriate aerogels the preparation of lotions, creams and gels with and without a peeling effect is also possible. Substances within the meaning of these applications are substances which can be used in pharmacy, e.g. pharmaceuticals, aromatic substances and flavorings.

The invention is described in greater detail in the following with the aid of working examples, without being restricted thereby.

PREPARATION EXAMPLES

Example 1
Preparation of a Permanently Hydrophobic Aerogel 1 l of a soda waterglass solution (with a content of 7% by weight of $SiO_2$ and an $Na_2O:SiO_2$ ratio of 1:3.3) was stirred together with 0.5 l of an acidic ion-exchange resin (styrene-divinylbenzene copolymer having sulfonic acid groups, commercially available under the name ®Duolite C20), until the pH of the aqueous solution was 2.3. The ion-exchange resin was then filtered off and the aqueous solution was adjusted to a pH of 5.0 using 1 molar NaOH solution. The resulting gel was then aged at 85° C. for a further 3 hours and the water was subsequently replaced by acetone using 3 l of acetone. The acetone-containing gel was then silylated with trimethylchlorosilane (5% by weight of trimethylchlorosilane per gram of wet gel). The gel was dried in air (3 hours at 40° C., then 2 hours at 50° C. and 12 hours at 150° C.).

The transparent aerogel thus obtained had a density of 0.15 g/cm$^3$, its specific surface according to BET was 480 m$^2$/g and it was permanently hydrophobic.

Example 2
Preparation of a Hydrophilic Aerogel

The permanently hydrophobic aerogel prepared in Example 1 was pyrolyzed for 1 hour at 600° C. in a gentle stream of air by means of a tube furnace. The transparent aerogel obtained had a density of 0.18 g/cm$^3$, a specific surface area according to BET of 450 m$^2$/g, and was hydrophilic.

USE EXAMPLES

In the use examples, hydrophilic and hydrophobic aerogels are employed such as were obtained according to Preparation Examples 1 and 2.

Example 1

| | Wettability of aerogels | |
|---|---|---|
| Aerogel | Hydrophilic | Hydrophobic |
| Acetone | + | + |
| Ethanol | + | + |
| Ethyl acetate | + | + |
| n-Hexane | + | + |
| Methanol | + | + |
| i-Propanol | + | + |
| Water | + | − |

+: wetting; −: no wetting

Example 2

Water absorption of aerogels during intensive mechanical incorporation

| | Water absorption (%) | Description |
|---|---|---|
| Aerogel, hydrophilic | up to 240 | free-flowing powder |
| | 280 | gelatinous consistency |
| | 300 | highly liquid suspension |
| Aerogel, hydrophobic | up to 140 | free-flowing powder |
| | 260 | viscous paste |
| | 320 | viscous white suspension |

Example 3
Loading of Aerogels with Na Carboxyfluorescein:

5 g of aerogel are treated with 50 ml of a 1.5% strength ethanolic Na carboxyfluorescein solution and the mixture is stirred for 2 hours. After filtration, the residue is dried at room temperature under normal pressure and the product is sieved. A free-flowing powder is obtained.

Content of Na carboxyfluoroscein
Aerogel, hydrophilic 6.2%
Aerogel, hydrophobic 5.7%
i.e. at least 38% of the amount of substance added is absorbed.

Example 4
Release of Na Carboxyfluoroscein from Aerogels:

Release apparatus: Paddle (USP)
Medium: Water, 37° C.

| Release Time (min) | 5 | 60 | 150 |
|---|---|---|---|
| Aerogel, hydrophilic | 51% | 80% | n.d. |
| Aerogel, hydrophobic | 13% | 18% | 38% |

Example 5
Loading of Aerogels with Pharmaceutical Active Compounds

Loading by suspending the excipient (aerogel, hydrophilic/hydrophobic) in an active compound solution and subsequent drying (normal pressure or reduced pressure) or application of an active compound solution to the dry excipient and subsequent afterdrying. A free-flowing powder is obtained.

A) Initially introduce 1 g of aerogel, add 20 ml of a 5% strength furosemide solution (acetone) with stirring, allow solvent to evaporate under normal pressure and at room temperature Active compound loading: 50%

B) Initially introduce 1 g of aerogel, add 2 ml of a 5% strength furosemide solution (acetone) with stirring, allow solvent to evaporate under normal pressure and at room temperature, repeat up to the desired loading (e.g. 4 times) Active compound loading: 33.3%

C) Initially introduce 1 g of aerogel, addition of a 5% furosemide solution (acetone) until a just -still flowable powder results, afterdrying (normal pressure or reduced pressure) Active compound loading: 13.0%

D) Initially introduce 1 g of aerogel, add 15 ml of a 1.3% strength furosemide-sodium solution (acetone) with stirring, allow solvent to evaporate at normal pressure and at room temperature Active compound loading: 16.6%

E) Initially introduce 1 g of aerogel, add 15 ml of a 1.3% strength penbutulol hemisulfate solution (methanol/ethanol 1:1) with stirring, allow solvent to evaporate at normal pressure and at room temperature Active compound loading: 16.6%

F) Initially introduce 1 g of aerogel, add 20 ml of a 1% strength HOE 277* solution (ethanol) with stirring, allow solvent to evaporate at normal pressure and at room temperature Active compound loading: 16.6%

* Pyridine-2,4-dicarboxylic acid N,N-(3-methoxypropyl)amide (described in EP-A-0 409 119)

G) Initially introduce 1 g of aerogel, add 13.5 ml of a 0.75% strength methylprednisolone solution (ethanol) with stirring, allow solvent to evaporate at normal pressure and at room temperature Active compound loading: 9.1%

Example 6

Release of Pharmaceutical Active Compounds from Aerogels

A) Release of methylprednisolone from hydrophobic aerogel
Loading: 9.1% methylprednisolone
Release method: Blade stirrer method GP 10
Medium: Hydrochloric acid 0.1 N

| Time (min) | Release of methyl-prednisolone pure substance (%) | Release of methyl-prednisolone from hydrophobic aerogel (%) |
|---|---|---|
| 15 | 18.8 | 16.8 |
| 120 | 84.1 | 41.1 |
| 480 | 91.5 | 58.7 |
| 1440 | 92.3 | 77.2 |

B) Release of methylprednisolone from aerogels
Loading: 9.1% methylprednisolone
Release method: Blade stirrer method GP 10
Medium: Phosphate buffer pH 7.5

| Time (min) | Release of methylprednisolone pure substance (%) | Release of methylprednisolone from hydrophilic aerogel % | Release of methylpednisolone from hydrophobic aerogel (%) |
|---|---|---|---|
| 3 | 3.9 | 56.5 | 1.6 |
| 6 | 12.5 | 68.2 | 3.1 |
| 15 | 33.2 | 75.3 | 6.5 |
| 30 | 53.9 | 78.6 | 11.6 |

C) Release of Hoe 277 from aerogels
Loading: 16.6% Hoe 277
Release method: Blade stirrer method GP 10
Medium: Hydrochloric acid 0.1 N

| Time (min) | Release of Hoe 277 from hydrophilic aerogel (%) | Release of Hoe 277 from hydrophobic aerogel (%) |
|---|---|---|
| 6 | 94.3 | 20.8 |
| 15 | 94.3 | 24.9 |
| 30 | 94.8 | 28.9 |

D) Release of furosemide from aerogels
Loading: 50% furosemide
Release method: Blade stirrer method GP 10
Medium: Water

| Time (min) | Release of furosemide pure substance (%) | Release of furosemide from hydrophobic aerogel (%) |
|---|---|---|
| 3 | 8.7 | 2.3 |
| 6 | 15.7 | 2.7 |
| 15 | 29.9 | 5.5 |
| 30 | 49.5 | 9.0 |

Example 7

Preparation of Aerogel Tablets:

| Recipe: | Microcryst. cellulose | 1 part |
|---|---|---|
| | Corn starch | 1 part |
| | Mg stearate | 0.01 parts |
| | Aerogel* | 0.05 parts |

*: Na carboxyfluorescein-containing aerogels from Ex. 3 (hydrophilic or hydrophobic)

Process: Mixing of the components and subsequent direct tableting using an eccentric tablet press to give round, biplanar tablets (Ø6 mm) having a mass of 100 mg and a radial compressive strength of 50 and 100 N.

Tablets can be prepared without problems using both hydrophilic and hydrophobic aerogels.

Example 8

Preparation of Aerogel Capsules:

| Recipe: | Aerogel* | 2 parts |
|---|---|---|
| | Lactose 1 H$_2$O D 80** | 98 parts |

*: Na carboxyfluorescein-containing aerogels from Ex. 3 (hydrophilic or hydrophobic)
**: Meggle, Wasserburg Process: manual filling
Both with hydrophilic and with hydrophobic aerogels, free-flowing powders are obtained which can be filled into capsules without problems.

Example 9 (a, b, c and d)

Preparation of Hydrophilic or Hydrophobic Aerogel Suppositories:

| Recipe: | Aerogel* | 2 parts |
|---|---|---|
| | Witepsol** | 98 parts |

*: Na carboxyfluorescein-containing aerogels from Ex. 3 (hydrophilic (a, b) or hydrophobic (c, d))
**: Witepsol H 12 (a, c) or Witepsol W 45 (b, d), Hüls AG, Witten Process: fusion molding process
The hydrophilic and hydrophobic aerogels can be incorporated without difficulties into the two suppository bases.

Example 10 (a, b, c and d):

Preparation of Water-Containing Aerogel Suppositories:

| Recipe: | Aerogel* | 1 part |
| --- | --- | --- |
| | Fluorescein sodium soln. 1.5% strength | 1 part |
| | Witepsol** | 98 parts |

*: Aerogels (hydrophilic (a, b) or hydrophobic (c, d))
**: Witepsol H 12 (a, c) or Witepsol W 45 (b, d), Hüls AG, Witten Process: fusion molding process The aqueous phase can be incorporated without difficulties into the two suppository bases.

Example 11

Preparation of an Aerogel Lotion:

| Recipe: | |
| --- | --- |
| Aerogel | 4.41 g |
| Propylene glycol | 8.82 g |
| Polysorbate 60 | 4.41 g |
| Polysorbate 65 | 4.41 g |
| Liquid paraffin, highly liquid | 13.24 g |
| Polyacrylic acid | 0.22 g |
| Sodium hydroxide solution 1 N | 0.88 g |
| Edetic acid, tetrasodium salt dihydrate | 0.09 g |
| Methyl 4-hydroxybenzoate | 0.10 g |
| Propyl 4-hydroxybenzoate | 0.01 g |
| Water | 63.41 g |

Both with the hydrophilic and with the hydrophobic aerogel, a white homogeneous milk with a peeling effect results.

Example 12 (a and b)

Preparation of Aerogel-Containing Gels

| Recipe: | Aerogel* | 11.0 g |
| --- | --- | --- |
| | Miglyol 812 | 99.0 g |

*: Aerogels (hydrophilic) (a) or hydrophobic (b))

Clear or slightly opalescent gels with a peeling effect result.

Example 13

Loading of Hydrophilic or Hydrophobic Aerogel with Lipophilic Substances

| Recipe: | Aerogel | 3 g |
| --- | --- | --- |
| | Sudan Red | 0.5 g |
| | Isopropanol | 80 g |

Sudan Red is dissolved in isopropanol and stirred with the appropriate aerogel for 2 hours. After separating off the excess, liquid phase, the aerogel is dried at room temperature and normal pressure. A free-flowing Sudan Red-containing powder is obtained.

Example 14

Dispersion of Lipophilic Substances in Hydrophilic Media

| A) Aerogel, *hydrophilic with Sudan Red | 1 part |
| --- | --- |
| Water | 99 parts |

A homogeneous red suspension is obtained. Agglomeration of particles is not observed.

| B) (Comparison example) | 0.1 parts |
| --- | --- |
| Sudan Red | |
| Water | 99 parts |

Even after intensive shaking no wetting or dispersion of Sudan Red in water takes place. The product agglomerates strongly.

| C) Aerogel, hydrophobic with Sudan Red | 1 part |
| --- | --- |
| Water | 99 parts |

A homogeneous dispersion of the Sudan Red-containing aerogel on the surface of the water is obtained without agglomerates occurring.

Example 15

Loading of Aerogel with Hydrophilic Substances

| | | hydrophobic | hydrophilic |
| --- | --- | --- | --- |
| Recipe | Aerogel | 1 part | 1 part |
| | Water | 1.4 parts | 2 parts |
| | Water content (%) | 58 | 66 |

After intensive trituration, a homogeneous free-flowing powder is obtained.

Example 16

Dispersion of Hydrophilic Substances in Hydrophobic Media

| A) Aerogel (water-containing) | 1 part |
| --- | --- |
| (hydrophilic or hydrophobic) | |
| Sesame oil | 50 parts |

A homogeneous, water-containing suspension is obtained with gentle stirring. Separation of water cannot be observed even after 24 hours.

| B) Water | 0.1 part |
| --- | --- |
| Sesame oil | 50 parts |

Even with vigorous stirring, homogeneous dispersion of the water (hydrophilic model substance) in sesame oil is not possible. After a short time, dispersed water droplets aggregate. There is always a clear phase separation.

Example 17
Preparation of Hydrophilic Aerogel Suppositories with an Included Hydrophilic Phase

| Recipe: | Aerogel, hydrophilic | 1 part |
|---|---|---|
| | Fluorescein Na soln. 1.5% strength | 2 parts |

After trituration, a free-flowing powder is obtained which can be incorporated up to a proportion of 33% ($\cong$22% of hydrophilic phase) without problems and homogeneously in molten suppository bases (Witepsol H 12 or W 45). No hydrophilic phase escapes from the suppositories. Witepsol H 12 suppositories with 5% sodium fluorescein solution (1.5% strength) however, are inhomogeneous. The hydrophilic phase escapes from the suppositories.

What is claimed is:

1. A pharmaceutical composition which comprises an pharmaceutical active agent and inorganic aerogel particles.

2. The pharmaceutical composition according to claim 1, wherein the composition is an accelerated release composition.

3. The pharmaceutical composition according to claim 1, wherein the composition is a controlled release composition.

4. The pharmaceutical composition according to claim 1, wherein the composition is a delayed release composition.

5. The pharmaceutical composition according to claim 1, wherein the composition is solid, semisolid or liquid composition oral administration.

6. The composition according to claim 1, wherein the composition is for topical administration of the active agent.

7. The composition according to claim 1, wherein the composition is for dermal, vaginal, rectal and oromucosal administration of the active agent.

8. The composition according to claim 1, wherein the aerogel particles have porosities of over 60% and densities under 0.6 g/cm$^2$.

9. The composition according to claim 1, wherein the composition float on gastric juice.

10. The composition according to claim 1, wherein the aerogel particles comprises SiO$_2$, A$_2$O$_3$, TiO$_2$, ZrO$_2$, or mixtures thereof and optionally have hydrophilic or hydrophobic surface groups.

11. In a process of preparing a pharmaceutical preparation, which comprises a pharmaceutical and at least one solid, liquid or gas substance in a solid or liquid media and has improved dispersant properties, the improvement which comprises adding inorganic aerogel particles as an auxiliary or excipient to a mixture comprising said pharmaceutical, said solid, liquid or gas substance or substances, and said solid or liquid media.

12. The process according to claim 11, wherein the aerogel particles have a porosity of over 60% and densities under 0.6 g/cm$^2$.

13. The process according to claim 11, wherein the preparation is liquid.

14. The process according to claim 11, wherein the preparation is a solid, semisolid or liquid oral preparation.

15. The process according to claim 11, wherein the preparation is for topical administration.

16. The process according to claim 11, wherein the preparation is for dermal, vaginal, rectal and oromucosal administration.

17. The process according to claim 11, wherein the preparation is for the accelerated, controlled or delayed release of pharmaceutical.

18. The process according to claim 11, wherein the preparation floats on gastric juice.

19. The process according to claim 11, wherein the inorganic aerogel particles comprise SiO$_2$, A$_2$O$_3$, TiO$_2$, ZrO$_2$, or mixture thereof and optionally have hydrophilic or hydrophobic surface groups.

20. A process for dispersing hydrophobic substance in hydrophilic media, which comprises incorporating the hydrophobic substance into inorganic aerogel particle and adding the particle into the hydrophilic media.

21. The process according to claim 18, wherein the substance is a pharmaceutical.

22. The process according to claim 20, wherein the inorganic aerogel particles have porosities over 60% and densities under 0.6 g/cm$^2$.

23. The process according to claim 20, wherein the inorganic aerogel particles comprise SiO$_2$, Al$_2$O$_3$, TiO$_2$, ZrO$_2$ or mixtures thereof and optionally have hydrophilic or hydrophobic surface groups.

24. A process for dispersing a hydrophilic substance in a hydrophobic media which comprises incorporating the hydrophilic substance into inorganic aerogel particles and adding the particles to the hydrophobic media.

25. The process according to claim 24, wherein the substance is a pharmaceutical.

26. The process according to claim 24, wherein the inorganic aerogel particles have porosities over 60% and densities under 0.6 g/cm$^2$.

27. The process according to claim 24, wherein the inorganic aerogel particles comprise Sio$_2$, Al$_2$O$_3$, TiO$_2$, ZrO$_2$ or mixtures thereof and optionally have hydrophilic or hydrophobic surface groups.

* * * * *